United States Patent [19]

Fisher

[11] Patent Number: 5,376,254

[45] Date of Patent: Dec. 27, 1994

[54] POTENTIOMETRIC ELECTROCHEMICAL DEVICE FOR QUALITATIVE AND QUANTITATIVE ANALYSIS

[76] Inventor: Arkady V. Fisher, 16191 W. Pope Blvd., Prairie View, Ill. 60069

[21] Appl. No.: 62,962

[22] Filed: May 14, 1993

[51] Int. Cl.$^5$ ............................................. G01N 27/26
[52] U.S. Cl. .................................... 204/416; 204/403; 204/435; 435/817; 422/82.03
[58] Field of Search ........................ 204/416, 403, 435; 435/817; 422/82.03

[56] References Cited

PUBLICATIONS

I. A. Gur'ev et al.; Zavodskaja laboratoria, 46, No. 6 497 (1980) ** Incorporated by reference in specification.

Primary Examiner—John Niebling
Assistant Examiner—Bruce F. Bell
Attorney, Agent, or Firm—John E. Vanderburgh

[57] ABSTRACT

An ion sensitive electrode device which consists of one or more ion-pairs distributed in at least one of two or more immiscible phases consisting of an aqueous phase, an organic phase, a polymer phase or a solid electrolyte phase. A reference solution includes an aqueous solution of the ion-pair and a high concentration of a micelle former such as an anionic or cationic detergent or a ligand. The device can be used to measure organic and inorganic compounds or can be readily modified by the addition of a biological material to the reference solution for the bioassay for bioorganic compounds.

36 Claims, 4 Drawing Sheets

POTENTIOMETRIC ELECTROCHEMICAL DEVICE FOR QUALITATIVE AND QUANTITATIVE ANALYSIS

FIELD OF THE INVENTION

This invention relates to an improved ion-selective electrode (ISE) biosensor having an ion-pair distributed between at least two phases.

BACKGROUND OF THE INVENTION

Ion selective electrodes (ISE) operate on the measurement of the potential created when the equilibrium between an ion-pair is unbalanced, such as for example by the presence of an ion which disturbs the equilibrium or a substance such as an antibody which reacts with an antigen to create a potential which disturbs the equilibrium, between the ion-pair. An ISE includes a reference solution which comprises an aqueous solution of electrolyte and an ion-pair which is only slightly soluble in the aqueous solution. An ISE is useful for the measurement of concentrations of substances which cannot be detected by electrodes that depend upon the ionization of the substance being measured. Accordingly an ISE is used for the measurement of the concentration of organic compounds in a test solution or, when suitably modified in a manner known in the art, for the detection of bio-compounds.

The concept of biosensor was proposed more than twenty years ago. Numerous papers and patents describing various biological compounds associated to several sophisticated types of transducers for the assay of a variety of analytes, were issued. Since then, however, only a few biosensor based analyzers have become commercially available. It appears that the most commonly used biosensor is the enzyme electrode and the transducer is the amperometric probe for oxygen or hydrogen peroxide detection associated to an immobilized oxidase. The main biological sensitive elements used for design of biosensors are: enzymes, antibodies, organelles, bacteria or whole cells or tissue slices. The transducers generally used for design of biosensors are: amperometric or potentiometric electrodes, field effect transistors, piezoelectric crystals, thermistors, optoelectronic systems. The commercially available biosensor are used to analyze the glucose, enzymes and enzyme substrates. The typical example of described biosensor is disclosed in U.S. Pat. No. 4,894,253, issued Jan. 16, 1990.

The aromatic sulphonate ion-selective electrode (ISE) has been used in the prior art, for example, for the analysis of anionic detergents. As set forth in *Talanta*, 20, p. 867 (1973) a nitrobenzene solution of benzene sulphonate crystal violet was used as a liquid organic phase. The lower part of a glass U-tube (50 ml capacity) was filled with an organic phase of an ion-pair. Reference and sample solutions were separated from the organic phase and they were aqueous solutions of the same sulphonate as in the liquid organic phase. The reference and sample solutions were connected to saturated calomel electrodes through an agar bridge saturated with potassium chloride. The ISE had an approximately Nernstian slope (56 mV/log C) down to $1 \times 10^{-4}$M and was useful to $1 \times 10^{-5}$M. However the cited ISE has undesirable limitations, for example, the ISE is not sensitive and reproducible enough; the U-tube construction of the ISE body has open excess to nitrobenzene what is not convenient for analytical measurements and hazardous to use ecologically; the liquid organic phase exposure to solution of interest is not acceptable for biosensor development and hazardous ecologically.

I. A. Gur'ev at al. disclosed improvements of existing ISE technology in "Simplified the Design of a Liquid Ion Selective Electrode", *Zavodskaja laboratoria*, 46, No. 6, 497 (1980). This ISE was also used for the analysis of anionic detergents, its ISE organic phase consisted of a nitrobenzene solution of lauryl sulphate and crystal violet. The ISE was made as an adaptor to the silver/silver chloride electrode and the second silver/silver chloride electrode was used to complete the circuit. The lower part of the plastic tube was filled with fluoropolymer (USSR Trademark Floroplast F-4) that was swelled in the liquid organic phase before putting it in the tube and then compressed into the end of the tip of the adaptor tube. The liquid organic phase comprising a nitrobenzene solution of ion-pair lauryl sulphate crystal violet was placed above the polymer phase. A reference solution of $1 \times 10^{-2}$M potassium chloride was used. The ISE had a Nernstian slope (59 mV/log C) down to $1 \times 10^{-6}$M and was useful to $1 \times 10^{-7}$M. The ISE is more convenient to use when it is in an adapter form. The sensitivity of the ISE was increased ten times. The limitations of the described development are: the reproducibility was improved but not sufficiently to market this analytical method; the liquid organic phase leaks through the polymer composite phase during ISE operation; and the estimated life of the ISE is only about six months. A. Fisher disclosed certain aspects of the described ISE in an article entitled; "The use of ISE in Waste Water Analysis", *The Method of Environmental Analysis*, Moscow, 140–141, (1983).

Most applications of the ISE involved the analysis of detergents, nitrates, nitrophenols, sulfides and other compounds in ground and waste waters. Later A. Fisher published two articles: "Study of the Mechanism of the Functioning of a Liquid Membrane of an ISE Based on Ion-Pair Lauryl Sulphate Crystal Violet.", and "Asymmetry Potential of an ISE with a liquid Organic Phase Based on Ion-Pair of Lauryl Sulphate Crystal Violet.", *Zhurnal Analyticheskoi Khimii.*, 40, No. 3, 5, 493–499, 935–936, 1985. The first article discusses the mechanism of the ISE functioning. In the second article it is disclosed that the ion-pair exists in the polymer composite phase in the form of liquid crystals.

Several articles are available on detergent electrodes with semipermeable phases and their use in the micelle cells. For example see: Kaibara K., et al. *Mem. Fac. Sci. Kyushu Univ.*, Ser. C, 7, 1, (1970); Botre C., at al., *Kolloid Z. Z. Polym.*, 250, 900, (1972); Birch B. J., at al., *Anal. Chim. Acta*, 69, 473, (1974); Senkyr J., *J. Chem. Listy*, 73, 1097, (1979). The ISEs constructed in accordance with the teachings of these articles have little selectivity and long response time. The last article describes an ISE with a liquid organic phase based on Crystal Violet which is used for nitrate analysis. This ISE has a concentration range $1 \times 10^{-7}$ to $1 \times 10^{-6}$M and a surfactant potentiator factor of 10 to 2.5M. However, because the liquid organic phase leaks from the ISE, the useful life of the module is about 6 months.

Despite a considerable amount of work applied to the development of electroanalytical devices which can be used in a ISE or biosensor mode a need still exists for an electrode, and a simple and inexpensive method for making it, which exhibits reproducible response, rapid response time, selectivity and sensitivity which can be miniaturized. In addition there exists a need for a commercial device for the detection and measurement of biocompounds.

SUMMARY OF THE INVENTION

It is an objective of the present invention to provide an electrode meeting the needs mentioned above and to further provide a method of making an electrode of any desired dimension in a simple and readily reproducible manner.

Another object of the invention is to provide a liquid crystal biosensor.

These and other objectives and advantages of the invention are achieved by an electrode which consists of two or more phases in any combination of phases comprising an aqueous reference solution phase, an organic phase (liquid or solid) and a polymer composite phase. At least one of the phases includes an ion-pair as described in more detail below. The polymer composite phase is comprised of a polymer matrix alone or with the liquid organic phase or a liquid crystal material suspended or dissolved therein. An ion-pair may also be included in the polymer composite phase of the electrode.

ISE devices constructed in accordance with the invention have several embodiments. In one embodiment the ISE is employed as an ion-selective electrode for the analysis of organic and inorganic compounds. In this embodiment ISE consists of the three phases, (1) an aqueous reference solution phase, (2) a liquid organic phase and (3) a polymer composite phase. The 3rd phase may or may not contain liquid organic phase to form a solid electrolyte. In this embodiment the ISE may be employed as a biosensor.

In another embodiment, the device of the invention is used as a self-rechargeable ISE. It has the same structure as the ISE in embodiment previously discussed, but there is special storage for the liquid organic phase or reference solution, which can be attached or detached to the device body.

In a third embodiment of the invention the ISE is disposable and consists of the three phases, (1) an aqueous reference solution phase, (2) a liquid organic phase and (3) a polymer composite phase which comprises a solid electrolyte.

In accordance with the invention the reference solution is an aqueous solution of an ion-pair and a high concentration of a ligand or detergent micelle former. The ion-pair is used in stoichiometric and non-stoichiometric forms and comprises a pair of oppositely charged ions. The ions forming the ion-pair are preferably large molecules having an association constant on the order of $1 \times 10^6$ to about $1 \times 10^{17}$. The formation and use of an ion-pair is well known in the art and does not per se form a part of the invention defined herein. However, the use of an ion-pair in an aqueous detergent solution to form the reference solution of electrodes constructed in accordance with the invention provides unexpected advantages over the prior art ISE.

The polymer composite phase was prepared from finely divided polymer which was swelled in a suitable solvent and then compressed into the end of the tip of a tube defining the body of the ISE. The ion-pair exists in the polymer composite phase in the form of liquid crystals. The solid electrolyte solution of the ion-pair was prepared by dissolving the ion-pair organic solvent solution in hot melted polymer. The solid electrolyte phase was used as a separation phase between the reference solution phase compartments in disposable devices. Another use of the solid electrolyte ion-pair phase is the support of the superthin composite phase in biosensor development. Another use of the solid electrolyte phase is the preparation of disposable ISEs. The body of the ISE can have any configuration. The body of the ISE can have special openings to join with syringes for recharging the reference solution or changing the liquid organic phase or reference solution without the necessity of disassembling and reassembling the ISE. This permits the ISE/biosensor to be made so that it can be assembled from disposable parts. In addition the electrode body can be shaped to reduce leakage of the liquid components of the electrode and thus increase the reliability and useful life of electrode constructed in accordance with the invention.

Devices constructed according to the invention are suitable for use as a non-permeable ISE which can have any structure described above. These biosensors can easily be manufactured and it is now possible to make stable biosensor interphases and to get reproducible potential readings. The biosensor does not need to be pre-calibrated and the customer can easily calibrate the biosensor at his site. The presence of biocompounds of interest, for example antigens, can be easily measured during biosensor calibration or during potential measurement. The biosensor is built from inexpensive organic materials. All parts of the biosensor can be easily and reproducibly fabricated. Each part of biosensor can be made disposable and can be easily shipped to the customer. Recharging can be easily done by a lab technician and no special training is required to use the biosensor. Although the biosensor is disposable, it can be used for several days without a fresh antibody recharge.

The advantages and features of the invention will be more fully understood from the detailed description of the invention taken in conjunction with the following drawings, brief descriptions of which are set forth below.

DETAILED DESCRIPTION OF THE INVENTION

Figure 1:
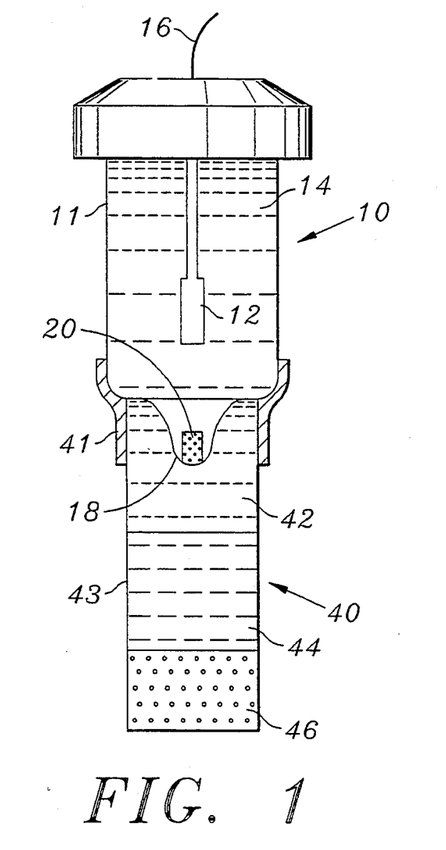
FIG. 1 is a schematic diagram of an ISE constructed in accordance with the invention.
Figure 2:
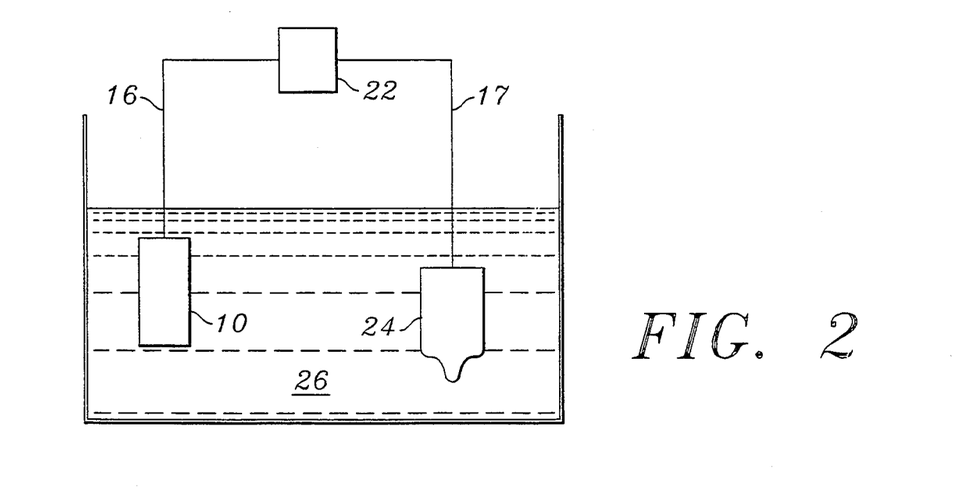
FIG. 2 is a schematic diagram of a typical circuit employing an ISE constructed in accordance with the present invention.

As illustrated by FIGS. 1 and 2, the ISE, shown generally as 10, comprises a hollow electrode body 11 in which is disposed a silver/silver chloride electrode 12 and a suitable electrolyte 14, for example an aqueous potassium chloride solution. An electrical conductor 16 extends from the electrode body 10 and is connected to a read-out device 22 which includes a conventional potentiometric reading and recording device or microprocessor, a power supply and amplifier and the like. The circuit is completed by a reference electrode 24, such as a silver/silver chloride electrode of conventional design, which is electrically connected to the read-out device by a line 17 and to the ISE 10 through a fluid 26 being tested.

As shown most clearly by FIG. 1, one end of the electrode body 11 defines an electrode tip 18. An electrically conductive bridge 20 is disposed in the tip for potentiometric communication with an ion selective electrode 40 (ISE) designed in accordance with the present invention and described in detail below. In the embodiments of the invention described herein the ISE 40 is provided with a sleeve 41 at one end to receive the tip 18 and end portion of the electrode body 11 for the attachment of the ISE 40 to the electrode body 11. However, other means may be employed to connect to electrode body 11 and the ISE 40 such as, for example, a flexible tube filled with a suitable electrolyte and sealed by electrolyte impermeable electrically conductive plugs of similar composition as the bridge 20 consists of an electrolyte impermeable ceramic plug well known in the art and commonly used with silver/silver chloride electrodes of conventional design.

In accordance with the invention the ISE 40 comprises a generally tubular body 43 in which are disposed three phases: a reference solution phase 42, a liquid organic phase 44 and a polymer composite phase 46. The polymer composite phase 46 further contains at least one of: (i) a polymer component alone; (ii) a liquid organic component consisting of an organic solvent distributed throughout the polymer matrix; (iii) a liquid crystal component consisting of a liquid crystal compound distributed throughout the polymer matrix and (iv) a solid electrolyte component consisting of an electrolyte distributed throughout the polymer matrix. When the polymer component is used alone it is preferred to introduce air to the liquid polymer to form pockets which are dispersed throughout the solid polymer. In this form the polymer can then be treated by heat or pressure or both to fill the air pockets with an electrolyte solution to substantially reduce the electrical resistance of the polymer.

The reference solution phase 42 directly interfaces with the liquid organic phase 44 which in turn directly interfaces with the polymer composite phase 46. The incompatibility of the respective phases maintains them in a generally separate condition although at the interfaces an equilibrium is established which is shifted by the presence of a sought for ion and which thus alters the potential of the electrode. It is also at the interface between the various phases that many of the problems associated with prior art ion selective electrodes occur.

The reference solution phase 42 comprises an ion-pair in an aqueous solution of a micelle former, such as for example an aqueous solution of a ligand or a detergent. It has been found that the presence of the micelle former helps to establish better distribution of the ion-pair between the reference solution and the organic phase of the electrode and reproducibility is enhanced and reproducibility of the ISE is substantially improved. Best results have been achieved when the concentration of micelle former in the reference solution is between about $1 \times 10^{-2}$ and $5 \times 10^{-3}$ mols/l.

Detergents used in the reference solution as the micelle former preferably have an alkyl chain of between 7 and 13 carbon atoms. It has been found that with smaller molecules, the detergent does not exert sufficient hydrophobicity to improve solubility ion-pair in the aqueous solution. Likewise if the backbone of the detergent molecule is too large solubility of the detergent in the aqueous solution is adversely affected. Best results have been achieved with detergents having a carbon chain of between 10 and 12 carbon atoms. Suitable detergents include the sulfonates, sulfoethers and phosphoric ethers having their carbon backbone as described above.

It should be noted that non-ionic detergents have no effect in the reference solution. Anionic detergents are preferred for use in the reference solution phase 42. The concentration of the detergent in the reference solution phase 42 is a matter of choice so long as it is maintained within the range described above. It should be noted that with higher detergent concentrations the potential becomes more reproducible and electrode sensitivity is reduced.

An ion-pair can be broadly defined as the association between two oppositely charged molecules. As applied to the present invention, an ion-pair consists of oppositely charged molecules (anionic/cationic) having an association constant in water of between $1 \times 10^6$ and $1 \times 10^{17}$. The molecules comprising the ion-pair may be organic, inorganic or combinations of the two. Ion-pair chemistry is well known in the art and any of the known ion-pairs can be used in the ISE of the present invention. For example the cationic molecule of the ion-pair include those based on triphenylmethane cations such as crystal violet, malachite green, methylene blue and methyl violet. Crystal violet is a preferred cationic molecule because it is one of the largest cationic molecules and it has a symmetrical structure, the importance of which is discussed below in connection with the liquid crystal phase of an ISE constructed according to this invention. The anionic component of the ion-pair is based on a molecular size sufficiently large to provide a large association constant yet small enough be slightly soluble in water. For example, the anionic component can include: organic compounds such as lauryl sulfate, cyanide, thiocyanate and nitrate; salicylic acid and salts thereof; picric acid and salts thereof; inorganic compounds such as negatively charged metal complexes such as gold and silver cyanide, thiocyanate. The liquid organic phase 44 comprises the ion-pair utilized in the reference solution phase 42 in an organic solvent. Although the molecules forming the ion-pair may be present in a stoichiometric ratio, preferably the ion-pair comprise the non-stoichiometric ratio of four mols of the anionic component to three mols of the cationic component. For example, in the case of the liquid organic phase 44 consisting of the ion-pair lauryl sulphate and crystal violet, in nitrobenzene. The distribution of lauryl sulphate in the two phase system nitrobenzene/water at the interface of the reference solution phase 42 and the liquid organic phase 44 is not stable and the ion-pair is drawn into the nitrobenzene resulting in eventual depletion of the ion-pair from the reference solution phase 42. The depletion of ion-pair is referred to herein as leakage. Such leakage of the ion-pair adversely affects the sensitivity and stability of the electrode. It has been found that the non-stoichiometric ratio of components in the ion-pair provides improved sensitivity and helps to stabilize the ion-pair in the respective phases. Also, because leakage of the ion-pair cannot be completely avoided, it is highly preferred that the volume of the reference solution phase 42 be substantially greater than the other phases of the electrode, on the order of at least three times greater than any of the other phases, so that leakage of the ion-pair does not deplete the ion-pair concentration in the aqueous reference solution.

The polymer composite phase 46 illustrated in FIG. 1 comprises a solid electrolyte component consisting of the ion-pair, lauryl sulphate and crystal violet, in nitrobenzene interspersed in a polypropylene matrix.

Figure 3:
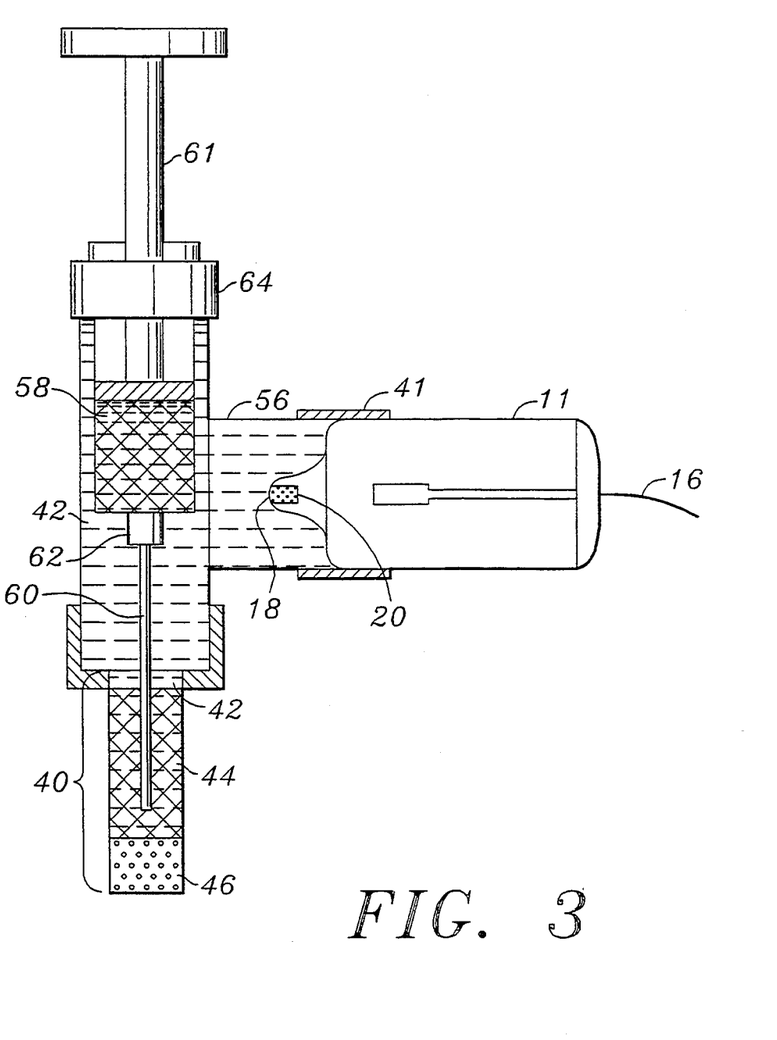
FIG. 3 is a schematic diagram of another embodiment of an ISE according to the invention illustrating a rechargeable ISE.

In the embodiment illustrated in FIG. 3, where like reference numbers designate like parts, the ISE is adapted for use as a self-rechargeable ion-selective electrode. In the device shown, the ISE 40 includes the reference solution phase 42, the liquid organic phase 44 and the polymer composite phase 46 as described in FIG. 1. The ISE 40 is adapted for recharge of the liquid organic phase by a normally extending chamber 56 which is connected to the silver/silver chloride electrode body 11 by the sleeve 41 and a liquid organic phase reservoir 58 within the reference solution phase 42. The reservoir 58 is closed at its upper end by a plunger 61. At the opposite end a small diameter silicon tube 60 is sealed to the reservoir 58 by suitable leak proof means such as a polymer plug 62. The reservoir is retained in the ISE 40 by a stopper or cap 64 which is preferably removable to facilitate replacement of the liquid organic phase. The liquid organic phase can be pushed out from the syringe to recharge the liquid organic phase 44 of the ISE 40 or drawn out to discharge the liquid organic phase 44.

During the operation and storage of an ISE the ion-pair, over a period of time, will be extracted from the reference solution phase 42 into the liquid organic phase 44 because the ion-pair is substantially more soluble in the organic solvent of the liquid organic phase 44 than in the aqueous reference solution of the reference solution phase 42. If the volumes of the phases are comparable this extraction affects ion-pair distribution and the potential of the ISE becomes unreproducible. In the preferred embodiment of the invention, the volume of the reference solution phase is substantially greater, on the order of three or more times, than the volume of the liquid organic phase 44 so that the ion-pair extraction can not affect the distribution of ion-pair between phases and the ISE has reproducible potential reading.

Figure 4:
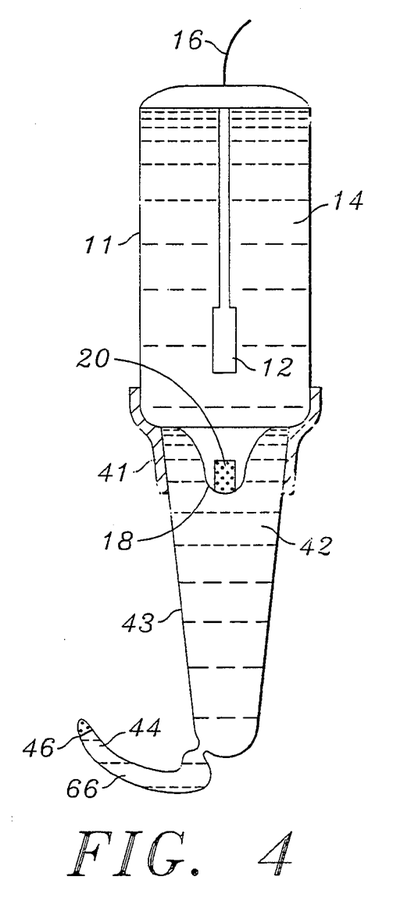
FIG. 4 is a schematic diagram of an ISE including a tip designed to reduce leakage of the liquid organic phase.

Another type of leakage problem encountered with ion sensitive electrode involves the passage of the organic solvent used in the liquid organic phase 44 of the ISE through the polymer composite phase 46 to the interface of the polymer composite phase 46 and the test fluid 26. This can be minimized by the embodiment of the ISE of the present invention illustrated in FIG. 4 where like reference numbers denote like parts in which a portion 66 of the tubular body 43 of the ISE 40 is formed back on itself to define a U-shape. It has been found that the U-shaped portion has a beneficial effect in reducing the leakage rate of the ISE 40.

The ion-pair solution of the reference solution phase 42 can be modified for detection of bioactive or other compounds. This modification can be achieved by directly adding a bioactive or other compound to the aqueous detergent solution of the ion-pair. An advantage of the aqueous detergent solutions is that bioactive compounds retain their bioactivity and stability. The highly aqueous detergent solution has been found to prolong the activity of bioactive compounds which can be deleteriously affected by the organic solvent of the liquid organic phase 44. Although not fully understood, it is believed that the detergent of the reference solution forms micelles which surround and shield the bioactive compound from the organic solvent. Therefore these compounds will be protected and the ionic charges can be transferred from one phase to another. If the ion-pair compound is present inside a micelle then the ion-pair helps to establish the conductivity of the micellic channel. If the bioactive compound is present in the micelle channel, the channel will have bioaffinity and conductivity. The micelle channel of the reference solution with antibody inside was used as a reference solution for an antigen biosensor.

The reference solution of the reference solution phase 42 of the ISE 40 can have an organic solvent as an additive to improve equilibrium stability. For example, where nitrobenzene is the solvent in the liquid organic phase 44 the additive is nitrobenzene. This addition was made to obtain the most stable equilibrium for a reproducible potential.

Micelles of amphophilic ions (lauryl sulphate) in high dielectric constant nonaqueous solvents (nitrobenzene) form reversed micelles. The aggregation number of lauryl sulphate is increased several orders of magnitude in a solution of an ion-pair because the solubility of an ion-pair in water is much lower compared to the solubility in a solution of lauryl sulphate. Although it is not fully understood, it is believed that aqueous detergent-/ion-pair micelles protect high molecular weight biologically active compounds and that this micellic protection of bioactive compounds is multi-layered because the hydrophobic parts of the detergent are directed inside the micelle. The transition of the aqueous micelle from the reference solution to a reversed micelle of the liquid organic phase is facilitated. The aqueous micelles are multilayered and are transferred from the reference solution to the liquid organic phase because of the affinity of the ion-pair for the organic solvent. When the micelles interact with the organic solvent they lose a layer and became reversed micelles. When the first layer is peeled off, the micelle will be transferred from direct to a reverse micellic structure in which compounds are shielded from the organic solvent. Therefore the bioactive compounds can exist and be transported by the organic solvent without destruction. In addition, this effect liberates the micelle covered biocompound, such as an antibody, and the liberated antibody can be immobilized in a liquid crystal component of the polymer composite phase 46, as will be described, to react with the antigen of the solution of interest. The lauryl sulphate crystal/violet ion-pair exists on the surface and in the inside of the polymer composite in the form of liquid crystals. Our measurements show that the diameter of the liquid crystal is about $4 \times 10^{-5}$ m. The liquid crystal can be used to insert the bioactive compound with an average molecular weight of $1 \times 10^7$ g. It is possible to measure the step or pitch of the liquid crystal spiral in a polarizing microscope photograph. It is about $2 \times 10^{-3}$ mm. This step can vary depending on the molecular insertion in the liquid crystal. A liquid crystal electrode is very effective as an ion-selective electrode or biosensor. The step of the spiral is equal to the size of detergent micelle. This helps bio-compounds keep their activity after insertion in liquid crystals.

The generation of potential by liquid crystals is associated with a molecular insertion in the liquid crystal spiral. It was expected that a biological compound can be immobilized inside a liquid crystal helix. This was shown by the insertion of an *E. coli* antibody during biosensor development. The phenomenon of insertion inside the liquid crystal is important for the following reasons:

a. The inserted compound can retain its activity inside the liquid crystal.

b. The changes in the charges of inserted compounds can be transferred from one side of the interface to another.

c. If the inserted compound will react with another compound (antibody will react with antigen) this will destroy the liquid crystal coverage of the inserted compound. This can generate a potential corresponding to this reaction or it can be used for quantitative measurement of molecules which produce a biosensor potential.

d. A very important characteristic of liquid crystals is their adjustment to many chemical structures. The spiral step can adjust to an antibody insertion.

Liquid crystals can be used to react with an antibody from the liquid organic phase using the antibody covered with mixed micelles. The antigen can react with the liquid crystal from the solution of interest.

An additional problem is related to the insertion of molecules into a liquid crystal helix. The inserted molecule affects the potential and after measurement it is difficult to get rid of the insertion. The next measurement will have more insertion and the potential will be affected again and the potential will be shifted even more than obtained with the same concentration of a compound of interest. The insertion capacity of liquid crystals is limited to a concentration level so when the liquid crystal is full of insertion the potential of the ISE will become reproducible.

As mentioned when the ion-pair is covered with detergent micelles it can be inserted in the liquid crystal in a stable way. A liquid crystal recharge solution was formulated. The composition of this solution was the same as the composition of the reference solution. The ion-pair was formulated in highly concentrated detergent solution. The same ion-pair concentration was used in the reference solution so that the ISE was kept equilibrated. The reproducibility was improved 7-8% for a direct concentration reading.

If the bioactive compound is inserted inside the liquid crystal it can react with some other compound covered or uncovered with micelles in the solution of interest. This discharge reaction can be used to rid the liquid organic phase of unwanted ions in the liquid crystal. This kind of liquid crystal chemistry is useful when an enzyme is inside the liquid crystal and a substrate with an inhibitor is present in the solution of interest. This can be used for inhibitor, poison, or contaminant analysis sensitive to a concentration from $1\times10^{-10}$ to $1\times10^{-15}$M. An example of the use of a discharge solution is the rinsing of the ISE in water after measurement so that the ISE can be prepared for the next reading.

Interphase problems relate to the electrode organic solvent leakage:.

1. It is important not to have any organic solvent leak from the biosensor because any leakage will destroy the bioactive compounds in the solution of interest and will limit the use of the biosensor for quantitative measurements.

2. A difficult problem of biosensor development is the penetration of the liquid organic phase through the polymer composite phase.

A bioactive compound is coated with micelles in the reference solution, organic solvent phase and liquid crystal. The coating will be lost, however, when the bioactive compound reacts with its reactant in the solution of interest. If the solution of interest contains an organic solvent the bioactivity of the compound will be lost. If the polymer composite phase is coated from the outside with the solid electrolyte the bioactivity is protected for it will not be possible for the liquid organic phase to penetrate through the solid electrolyte phase and the bioactivity will be maintained.

An ISE can be stored in open air. Presumably this is the only electrode which can be stored in this way. However, the ISE should be stored without the liquid organic phase being in contact with the polymer phase because the nitrobenzene will evaporate in the open air and the ion-pair will precipitate in and on the polymer composite phase. This can limit the sensitivity of the ISE. The sensitivity can be easily restored by removing the precipitated ion-pair. The ion-pair precipitation within and on the organic phase surface is not liquid crystals and cannot be used as liquid crystals.

The precipitation described previously always occurred in the working biosensor because the ion-pair solution inside the liquid organic phase was oversaturated. Because of the limited volume of the polymer composite phase, disposable biosensors are preferred.

The most important characteristic of the biosensor is its high sensitivity. The potential of the biosensor from an antibody-antigen interaction is a small part of the general potential. In order to increase the sensitivity of the biosensor the thickness of polymer phase must be decreased. In a working model the thickness was decreased to $1\times10^{-3}$ mm. The *E. coli* biosensor is sensitive to $1\times10^{4}$ bacteria. The sensitivity is due to the quality of the reference solution, liquid organic phase, liquid crystals and the method of their use. The sensitivity depends on the affinity of the antibody for the antigen. If it is necessary to analyze low concentrations of antigen solutions the theoretical concentration of the antibody in the liquid organic phase can be approximated by thermodynamic considerations. Some antigens can be detected at $1\times10^{-12}$ to $1\times10^{-15}$M.

The ISE of this invention can be used in the microelectrode mode. When used in this fashion, it is important to generate the maximum electric current through the organic phase and polymer composite phase. In order to develop the biosensor with maximum current the polymer composite phase thickness and diameter were decreased.

EXAMPLE 1

The following illustrates the construction and operation of a sensitive ion-selective electrode in accordance with the invention and its operation.

Ag/AgCl reference electrodes with ceramic junction and device for potential measurement pH/ion/temp meter with BNC electrode adaptor were obtained from Cole Palmer Instrument Co. The Ag/AgCl reference electrodes were used in a sealed condition, no additional recharge of saturated potassium chloride solution is required. The Ag/AgCl reference electrode used a $1 \times 10^{-2}$M solution of potassium chloride is the electrolyte.

The reference solution for the ISE reference solution phase of the electrode was prepared by forming a solution consisting of a $1 \times 10^{-3}$M solution of the ion-pair lauryl sulfate (LS) and crystal violet (CV) in $1 \times 10^{-2}$M aqueous solution of lauryl sulphate. The ion-pair had a mol ratio of components LS:CV=4:3. Lauryl sulfate sodium salt (LS) and crystal violet chloride salt (CV) were purchased from Aldrich Chemical Co. Before use the lauryl sulfate sodium salt was recrystallized three times from ethyl alcohol. The crystal violet chloride salt before use was recrystallized 15 times from water. The solutions of lauryl sulphate (LS) and crystal violet (CV) were prepared using double distilled water.

Preferably the composition ion-pair of the liquid organic phase is substantially the same as the reference solution. The organic solvent was nitrobenzene and the ion-pair consisted of equal parts of lauryl sulphate sodium salt and crystal violet chloride salt.

After preparation of the liquid organic phase it is possible to prepare the polymer phase of the ISE. A polyfluoroethylene polymer (Du Pont 7-A) was used in the powder form. 200 mg of the fluoroethylene powder and 1 ml of liquid organic phase prepared as described above was placed in a disposable glass tube and shaken by using a shaker for at least five minutes until a uniform suspension of polymer in the liquid organic phase was obtained. The suspension was poured into a plastic tube which serves as the electrode body and compressed into the tip of the polymer tube. The ISE body can be made out of a plastic shield for disposable syringe needles, for example a shield for syringe needles. The length of the tip was 5 cm, the bottom diameter of the tip was 4 mm. The bottom part of the tip was cut with a sharp knife, then the inside of the tip was scratched with a thin needle in order to keep the hard polymer phase after compression. The polymer liquid phase suspension is added to the tip. Usually a spatula was used to transfer the suspension from the glass disposable tube to the plastic tip. The electrode body was fixed in a holder in vertical position with the bottom part of the body with the suspension placed down. A metal shaft was inserted into the tube and used to compress the suspension contained therein to make the polymer phase. When the polymer phase was made 0.1 ml of liquid organic phase was added to the tube and finally 0.3 ml of the reference solution to form the reference solution phase. The ISE was connected to the Ag/AgCl electrode in the manner described above for FIG. 1 using a section of rubber tubing as the sleeve connecting the ISE and the Ag/AgCl electrode. Then the circuit was completed by using a second Ag/AgCl electrode in the manner shown in FIG. 2.

In order to evaluate the working device, the electrodes produced were used for measurement of the potential of different water based solutions of interest. In order to make the calibration of the electrode several solutions of detergents (lauryl sulfate) were prepared with concentrations pX$=-$log X$=$3, 4, 5, 6, 7, 8 and 10; $-$log X$=-$log [LS (M)]

Figure 5:
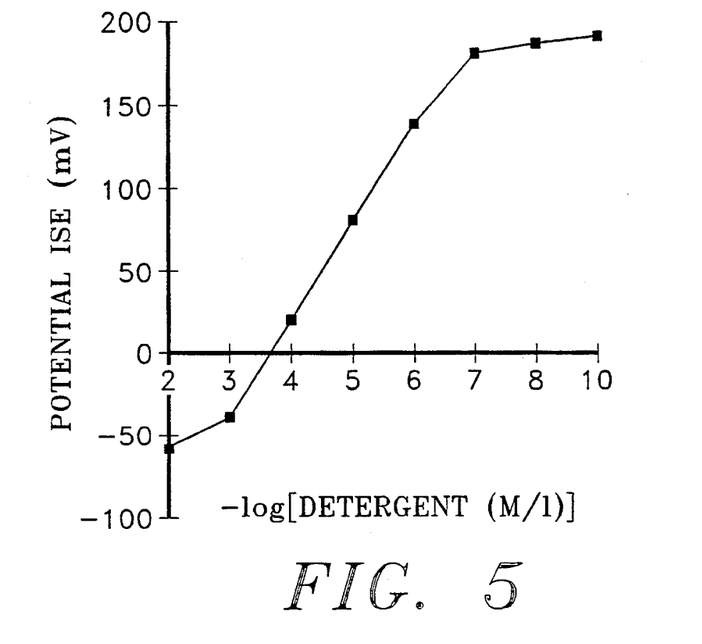
FIG. 5 is a plot potential vs detergent concentration (−log) and is a calibration curve for an ISE made in accordance with Example 1.

By measuring the potentials of these solutions it was possible to establish a calibration of the ISE. The calibration curve for the ISE is set out in FIG. 5 which is a plot of potential in millivolts plotted against $-$log X. It will be seen that excellent linearity is achieved at detergent concentrations of between $-$log 3 and $-$log 7. Any of the foregoing detergent solutions can be used as a control to check the correct reading during the analysis of an unknown.

The ISE exhibited excellent reproducibility with no leakage of nitrobenzene and a useful life in excess of 6 months.

EXAMPLE 2

The following example describes a rechargeable ISE made in accordance with the invention and a method of utilizing the rechargeable ISE in a sequential operation, such as a work station where repeated readings are taken or for use with different reference solutions was constructed and operated in accordance with the following. The recharge solution has the same composition as the liquid organic phase of the electrode.

The reference solution phase, liquid organic phase and polymer composite phase of the ISE were prepared as described in Example 1. The ratio of the ion-pair components in the liquid organic phase is LS:CV=4:3. The electrode body was provided with a reservoir as described above in connection with FIG. 3. The recharge solution consisted of $1 \times 10^{-3}$M solution of the ion-pair lauryl sulfate/crystal violet in the mol ratio of LS:CV=4:3.

Reproducibility of 7% for direct concentration reading and no penetration of nitrobenzene during potential measurement with a sensitivity of $1 \times 10^{-6}$M was attained.

The ISE was recharged after the 1st potential measurement according to the following procedure.

1. The ISE was rinsed in distilled water until the potential was stable. Usually this requires from one to three rinsings to reach stable potential. It takes one to two minutes to complete the measurements.

2. 1st solution potential measurement was taken. Instead of one concentration measurement it was found advantageous to take a set of four detergent concentration measurements ($1 \times 10^{-4}$M, $1 \times 10^{-5}$M, $1 \times 10^{-6}$M) for one ISE calibration. The calibration can be made for any ion of interest, which is active in the ISE.

3. The rinsing of the ISE in distilled water is the same as in paragraph 1.

4. Following rinsing, the ISE was recharged and the potential of the recharge solution was stablized. Usually the recharge potential of electrode varies in the range from 10 to 5 mV, depending on the condition of the electrode active surface. It takes usually one minute to complete the ISE recharge.

5. The discharge of the ISE in water is carried out as in paragraphs 1 and 2.

6. A 2nd solution potential measurement carried out in the same manner as in paragraph 2. The sequence of measurements from paragraph 1 to paragraph 3 will be the same for the 3rd concentration measurement.

In order to demonstrate the reproducibility of the ISE several sequences of calibration in lauryl sulphate solutions were made. This ISE had very good precision. For most measurements precision was between 2.0 and 5.6% for direct concentration reading. Some measurements had precision less than 1%, and shows the possibility of improving the existing level of precision. This improvement can be done if the ISE is used as a sensor element of the workstation. In this case it is possible to fix every ISE working parameter: to have the same speed and gradients of stirring in every measurement of every sample, to have the same hydrostatic regime in every measurement of every sample and some other technical and service related problems.

EXAMPLE 3

The following example describes the construction and operation of a rechargeable ion selective microelectrode. The electrode body is as described in Example 2 and includes a reservoir for the storage of the recharge solution.

The liquid organic phase ratio of components in the liquid organic phase is LS:CV=4:3. The method of preparing the reference solution phase, the liquid organic phase and polymer phase development is described in Example 1. The preparation of recharge solution is as described reference solution of Example 1.

The ISE was greatly decreased in size. The microelectrode is prepared by forming an ion selective adapter using the microfabrication technique set forth below:

1. 1 ml of the liquid organic phase was placed in a disposable glass tube and the tube was closed the tube with cork in order not to have escaping fumes.
2. 200 mg of polyfluoroethylene fine powder was added to the tube.
3. The tube was shaken thoroughly for fifteen minutes to thoroughly mix the contents and to suspend the PFE powder in the organic phase.
4. A disposable polypropelene tip from pipet (Baxter, Scientific Products Cat, diameter 0.3 mm) was placed in the tube and shaken at high speed for two minutes to cause the suspension to penetrate in the tip. The suspension is held in the tip by capillary force. The height of the suspension in the capillary was about 5 mm.
5. The polymer tip was removed from the glass tube and taking care that the suspension remains in the bore of the tip.* The end of the tip to the paper filter and at the same time hold the tip in the vertical position (liquid organic phase part to the bottom). Wait until the part of liquid organic phase will be taken out and absorbed by filter paper. When the height of the capillary will be about 3 mm. In this case some polymer phase layers are already formed inside the capillary.
6. Compression of the suspension within the tip:
   a. Fix the tip in the holder in vertical condition. The bottom part of the tip with suspension was placed down.
   b. A thin rod having an O.D. smaller than the bore of the tip containing the suspension was used for the compression step. This rod was made of steel 0.3 mm diameter and 15 cm long. The end of the rod was provided with a projection $6 \times 10^{-2}$ mm in diameter and a having a length of about 0.1 mm. This kind of projection will create an indentation in the polymer composite phase, which was used as a micro superthin polymer phase. Then the bottom part of suspension in the plastic tip was compressed with the shaft to form the compressed polymer phase. The height of the polymer phase is from 0.3 to 0.5 mm.
   c. All traces of the liquid organic phase suspension which were not incorporated in the polymer phase were removed from the electrode body by using an absorbent napkin.

Following preparation of the polymer composite phase, 0.005 ml of the nitrobenzene solution of lauryl sulfate/crystal violet as prepared in Example 1 was introduced over the polymer layer to form the liquid organic phase followed by 0.3 ml of the reference solution of Example 1 to form the reference solution phase of the electrode. The microelectrode ion selective adapter thus produced was connected to an Ag/AgCl as described in Example 1 using a piece of rubber tubing on top part of adaptor and the bottom part of the Ag-/AgCl electrode as shown in FIG. 1.

With the microelectrode it is possible to analyze smaller volumes of liquid. The micro ISE is inexpensive to manufacture and it is possible to mass produce it.

EXAMPLE 4

The following example illustrates an electrode constructed in accordance with the invention in which the polymer composite phase comprises a solid electrolyte component. The ISE having the solid electrolyte component has been successfully used for detergent analysis.

The ISE electrode was prepared as in Example 1 and consisted of a silver/silver chloride electrode attached to the plastic body of the ISE, which is filled with the reference solution of Example 1. The bottom the plastic body is covered with a solid electrolyte polymer component prepared according to this Example. The solid electrolyte polymer component comprises the polymer composite phase and also serves the function of the liquid organic phase of the ISE of Example 1.

Figure 6:
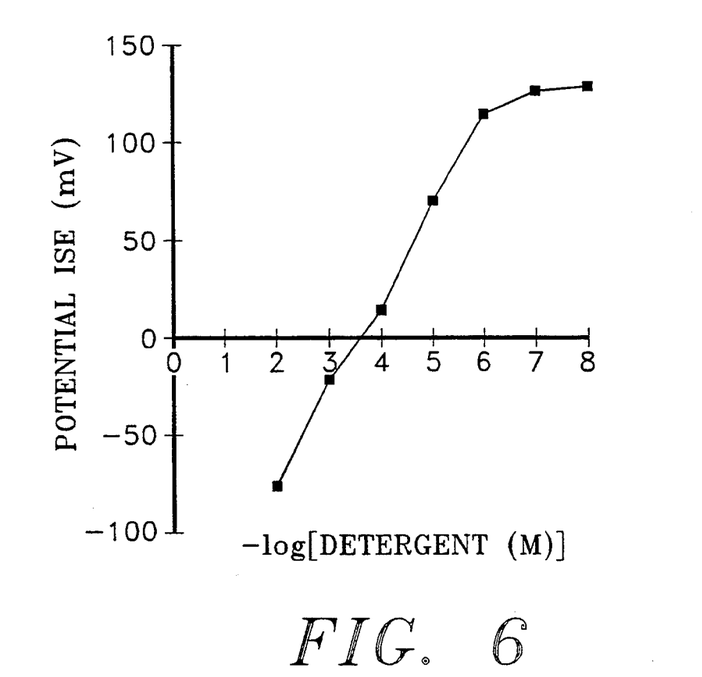
FIG. 6 is a plot potential vs detergent concentration (−log) and is a calibration curve for an ISE made in accordance with Example 4.

The liquid organic phase solid electrolyte was prepared by using a polypropylene disposable tip 2 ml capacity (B/D Life Science). The length of the tube was 85 mm, outside diameter was 5 mm. The end of the polypropylene tip was melted and the tube was closed. In the tube was added 0.3 ml of liquid organic phase prepared in accordance with Example 1. Then the tube with the liquid organic phase was heated to melt the polymer. The liquid organic phase was dissolved in hot polymer. A drop of melted polymer with liquid organic phase dissolved was set on one end of the plastic tube defining the ISE body and allowed to solidify and to close the end of the tube to define the tip of the ISE. The solid polymer on the tip was abraded to the point when the solid electrolyte electrode became electroconductive and its potential reading became reproducible (a thickness between $2 \times 10^{-1}$ mm and $1 \times 10^{-1}$ mm). Reference solution was added to the tube to constitute the reference solution phase of the ISE and the tube was connected to the silver/silver chloride electrode as described in Example 1 and shown in FIG. 1. Calibration of the electrode was carried out in the same manner as in Example 1 by preparing several solutions of detergent (lauryl sulfate) with concentrations pX=$-\log$ X=3, 4, 5, 6, 7, 8 and 10; $-\log$ X=$-\log$ [LS (M)]. The potentials of these solutions were measured and a plot of potential in millivolts plotted against $-\log$ X is shown in FIG. 6.

The electrode has very good response in a detergent concentration range from $1 \times 10^{-6}$ to $1 \times 10^{-3}$M with the slope of 65 mV per decade. The time of response is about one minute.

EXAMPLE 5

A method to prepare a reference solution for *E. coli* bioassay is illustrated by this Example.

The composition of reference solution should be close to the composition of liquid organic phase. In preparing the reference solution, the composition of liquid organic phase was a $1 \times 10^{-3}$M solution of an ion-pair in nitrobenzene; the ion-pair having a ratio of components LS:CV=4:3. The composition of the new reference solution is a $1 \times 10^{-3}$M solution of ion-pair in $1 \times 10^{-2}$M aqueous solution of lauryl sulphate and the ion-pair had a ratio of components LS:CV=4:3. The new reference solution is an aqueous high concentration detergent solution of an ion-pair.

The reference solution was modified for use as a reference solution in a biosensor for $E.\ coli$. 1/12th part of a lyophilized tablet of $E.\ coli$ bacteria antibody (purchased from Kirkegaard & Perry Chemical Co.) was dissolved 0.1 mL of 1:1 mixture of Glycerine and water and 0.1 mL of this solution was mixed with 0.5 mL of a detergent ion pair solution described previously. The final concentration of the ion-pair in the biosensor reference solution was $1 \times 10^{-4}$M and the final concentration of the $E.\ coli$ antibody was $1.38 \times 10^{-8}$M. The antibody in the biosensor reference solution was active for several days.

EXAMPLE 6

This example illustrates the construction and use of the ISE for the detection and measurement of antigens. The ISE was constructed in the manner described above in Example 4 using a polyfluoroethylene polymer melted in the presence of the liquid organic phase material of Example 1 to close the tip of the ISE plastic tube and to serve as the polymer composite phase.

0.3 ml of the liquid organic phase of Example 1 was introduced to the ISE tube. The reference solution of Example 5 was used so that the ISE would detect $E.\ coli$. The $E.\ coli$ biosensor is sensitive to $1 \times 10^4$ of the bacteria.

ISE sensitivity is based on the quality of the reference solution, liquid organic phase, liquid crystals and the method of their use. The most important parameter responsible for sensitivity is the affinity constant of antibody antigen interaction. From thermodynamic considerations it was found that in order to analyze low concentrations of antigen solutions in the liquid organic phase there needs to be created a high concentration of antibody 10. For some antigens it is possible to reach $1 \times 10^{-12}$ to $1 \times 10^{-15}$M detection limits.

Figure 7:
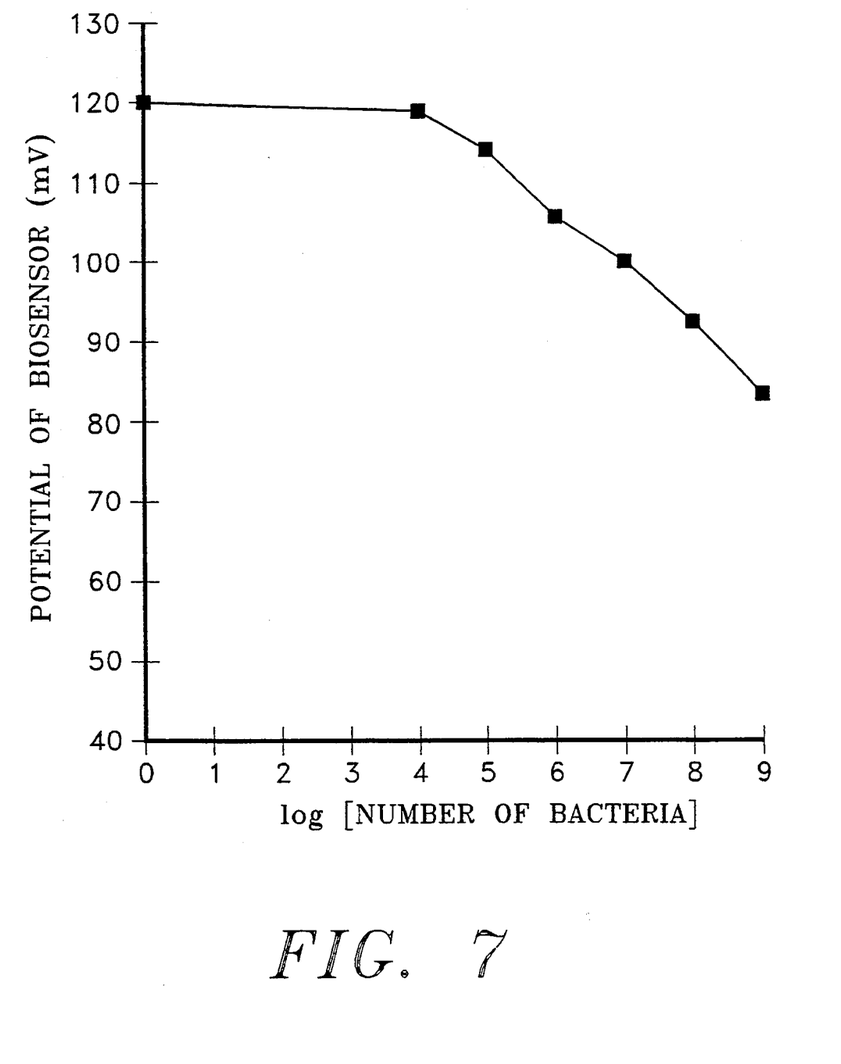
FIG. 7 is a plot potential vs bacteria concentration (+log) and is a calibration curve for an ISE made in accordance with Example 6.

As shown in FIG. 7, the $E.\ coli$ biosensor had a response to $E.\ coli$ bacteria from $10^4$ to $10^9$ $E.\ coli$ bacteria. The millivolt response of the biosensor is from 34 to 92 mV but this response depends on accuracy and precision in microfabrication. The biosensor can be developed not only for $E.\ coli$ bacteria but for others as well or other antigens depending upon the antibody added to the reference solution phase of the electrode.

Biosensors made in accordance with the invention can be easily manufactured using existing technology. It is possible to make a stable biosensor/liquid organic phase composition and to get a reproducible potential reading. The biosensor does not need to be precalibrated after development and can be easily shipped. The customer can easy calibrate it in his facility. The insertion of biocompounds of interest (antigen) outside the liquid organic phase can be easily done during biosensor calibration or during potential measurement. The biosensor is built out of organic material, all parts of biosensor composition can be easily made in reproducible way. The electronic equipment which was used to read the potential is the simplest pH/ionmeter one of the most inexpensive devices on the market. Each part of biosensor is disposable and can be shipped to the customer separately. The recharge can be very easily done by the customer or lab technician. No advanced education or special training is required to use the biosensor.

Ion selective electrodes constructed in accordance with the invention may be completely or partially disposable. This is particularly desirable for the construction of an ISE having a disposable tip which can be removed and exchanged for a different tip when testing for a different substance or when it is desired to switch from a biosensor to conventional ISE without the need to change the entire electrode setup.

The ion-selective electrode of the invention has particular utility as a sensor for organic and inorganic compounds or as a biosensor for the detection of antigens, antibodies, enzymes, microorganisms, substrates, hormones, receptors, or other bioorganic entities. The method of producing an electrode/biosensor in accordance with the invention is simple and inexpensive in comparison to prior art practices. The method is adapted to the fabrication of miniaturized or disposable electrodes or biosensors which have features generally recognized as being desirable but not hitherto attainable. The ion-selective electrode sensor of the invention has a ten times higher sensitivity compared to presently existing sensors and has several other advantages over existing electrodes: the ISE has no leakage from the organic phase, therefore the organic phase does not pose an environmental hazard; the ISE has better reproducibility and sensitivity; the ISE can be modified for use as a biosensor and both can be built as disposable devices.

As will be understood by those skilled in the art, various arrangements other than those described in detail in the specification will occur to those persons skilled in the art which arrangements lie within the spirit and scope of the invention. It is therefor to be understood that the invention is to be limited only by the claims appended hereto.

Having described the invention, I claim:

1. An improved ion selective electrode device for the potentiometric determination inorganic, organic and biological compounds in a liquid, said electrode comprising:

a. a reference electrode portion comprising a hollow electrode body in which is disposed an electrode in electrical communication with means for indicating potential and an electrolyte surrounding said electrode, said electrode portion including an electrically conductive bridge;

b. an ion selective portion comprising a hollow body defining an interior, said interior including at least two immiscible phases selected from the group consisting of an reference solution phase comprising an aqueous solution of a micelle forming agent and an ion pair, an organic phase and a polymer composite phase, at least one of said organic and polymer composite phases containing an ion-pair; and c. said ion selective portion being affixed to said reference electrode portion for electrical communication between one of said phases and said reference electrode portion through said bridge.

2. The ion selective electrode of claim 1 wherein said micelle forming agent is selected from the group consisting of ligands, anionic detergents, cationic detergents and combinations thereof.

3. The ion selective electrode of claim 2 wherein said reference solution comprises an aqueous detergent solution.

4. The ion selective electrode of claim 1 wherein said ion-pair is present in said organic phase.

5. The ion selective electrode of claim 1 wherein said ion-pair comprises molecules having an association constant on the order of $1 \times 10^6$ to about $1 \times 10^{17}$.

6. The ion selective electrode device of claim 1 wherein said ion-pair consists of lauryl sulfate and crystal violet.

7. The ion selective electrode device of claim 6 wherein said ion pair is present in said reference solution phase in the ratio of 4 mols of lauryl sulfate to 3 mols of crystal violet.

8. The ion selective electrode of claim 1 wherein said organic phase is a solid.

9. The ion selective electrode device of claim 8 wherein said ion pair is present in said organic phase in the ratio of 4 mols of lauryl sulfate to 3 mols of crystal violet.

10. The ion selective electrode of claim 8 wherein said micelle forming agent is a detergent having an association constant on the order of $1 \times 10^6$ to about $1 \times 10^{17}$ and an alkyl chain of between 7 and 13 carbon atoms.

11. The ion selective electrode of claim 10 wherein said detergent is lauryl sulfate.

12. The ion selective electrode of claim 1 wherein said organic phase is a liquid.

13. The ion selective electrode device of claim 1 wherein said device is adapted for use as a biosensor for the determination of a biological substance by the incorporation in said reference solution phase of a substance which is responsive to said biological substance being determined.

14. The ion selective electrode of claim 1 wherein said aqueous reference solution phase comprises said ion-pair in an aqueous detergent solution, said detergent having a concentration of between about $1 \times 10^{-2}$ and $5 \times 10^{-3}$ mols/l.

15. The ion selective electrode device of claim 14 wherein said biological substance being determined is E. coli and said reference solution contains E. coli antibody.

16. The ion selective electrode device of claim 13 wherein said reference solution contains about $1.38 \times 10^{-8}$ of E. coli antibody and said electrode detects E. coli bacteria in the range of between about $1 \times 10^4$ and about $1 \times 10^{10}$ of said bacteria.

17. The ion selective electrode of claim 1 wherein said polymer composite phase comprises at least one of:
   b. a liquid organic component consisting of an organic solvent distributed throughout the polymer matrix;
   c. a liquid crystal component consisting of a liquid crystal compound distributed throughout the polymer matrix; and
   d. a solid electrolyte component consisting of an electrolyte distributed throughout the polymer matrix.

18. The ion selective electrode of claim 17 wherein said polymer is selected from the group consisting of polyethylene, polypropylene and the halogen substituted products thereof.

19. The ion selective electrode device of claim 17 wherein said polymer composite phase incorporates a liquid crystal compound selected from the group consisting of nematic and cholesteric compound.

20. The ion selective electrode device of claim 17 wherein said liquid crystal compound comprises said ion-pair.

21. The ion selective electrode device of claim 17 wherein said polymer composite phase further includes a liquid polymer component comprising a matrix of polyfluoroethylene in which nitrobenzene is dispersed.

22. The ion selective electrode device of claim 17 wherein said polymer composite phase further includes a solid electrolyte component consisting of liquid organic phase dispersed throughout said polymer matrix.

23. The ion selective electrode of claim 17 wherein said polymer composite phase consists of a fluoropolymer having air pockets dispersed therethrough.

24. The ion selective electrode of claim 23 wherein said fluoropolymer is fluoroethylene.

25. The ion selective electrode of claim 23 wherein said air pockets are filled with an electrolyte solution thereby to lower the electrical resistance of said polymer composite phase.

26. The ion selective electrode device of claim 1 wherein said body of said electrode includes means for the ingress and egress of said reference solution phase whereby said reference solution phase is added and withdrawn from said electrode body.

27. The ion selective electrode of claim 1 wherein said electrode body further includes a separate reservoir in communication with said liquid organic phase and means for causing the transport of liquid organic phase between said reservoir and said electrode body.

28. The ion selective electrode device of claim 1 wherein said liquid organic phase comprises nitrobenzene in which said ion-pair is dissolved.

29. The ion selective electrode of claim 1 wherein said electrode body comprises two electrode portions, a first portion comprising said reference solution phase said first portion being connected at one end to said reference electrode and closed at the opposite end by said polymer composite phase and a second removable portion comprising a second hollow body comprising at least said polymer composite phase, said second portion being adapted for removable connection to said first portion, said polymer composite phase closing said first electrode portion providing electrical communication between said first and said second electrode portions.

30. The ion selective electrode of claim 1 wherein a portion of said body of said electrode is U-shaped thereby to reduce leakage of said ion-pair from one phase to another phase.

31. A reference solution for an ion sensitive electrode comprising an aqueous solution of an ion-pair and a micelle forming agent selected from the group consisting of ligands, anionic detergents, cationic detergents and combinations thereof.

32. The reference solution of claim 31 wherein the concentration of micelle former in the reference solution is between about $1 \times 10^{-2}$ and $5 \times 10^{-3}$ mols/l.

33. The reference solution of claim 31 wherein said micelle former is a detergent selected from the group consisting of anionic and cationic detergent compositions having an alkyl chain of between 7 and 13 carbon atoms.

34. The reference solution of claim 33 wherein said detergent composition is selected from the group of detergent compositions consisting of sulfonates, sulfoethers and phosphoric ethers having an alkyl chain of between 10 and 12 carbon atoms.

35. The reference solution of claim 31 further including a substance interactive with a material to be determined whereby said reference solution is responsive to the presence of said material to be determined.

36. The reference solution of claim 35 wherein said substance is E. coli bacterium.

* * * * *